United States Patent
Albini et al.

(10) Patent No.: US 6,815,422 B2
(45) Date of Patent: Nov. 9, 2004

(54) MOLECULES WITH ANTI-INFLAMMATORY ACTIVITY

(75) Inventors: Adriana Albini, Genoa (IT); Douglas Noonan, Genoa (IT); Roberto Benelli, Genoa (IT); Fabio Carrozzino, Genoa (IT); Leonardo Santi, Genoa (IT)

(73) Assignee: Centro Biotechnologie Avanzate, Genoa (IT)

( * ) Notice: Subject to any disclaimer, the term of this patent is extended or adjusted under 35 U.S.C. 154(b) by 0 days.

(21) Appl. No.: 10/255,096

(22) Filed: Sep. 26, 2002

(65) Prior Publication Data

US 2003/0064930 A1 Apr. 3, 2003

(51) Int. Cl.[7] .............................................. A61K 38/00
(52) U.S. Cl. ..................... 514/12; 530/350; 424/85.7
(58) Field of Search ........................... 514/12; 530/350; 424/85.7; 435/69.2

(56) References Cited

U.S. PATENT DOCUMENTS 6,544,761 B2 * 4/2003 Greene et al. ............. 435/69.2
6,576,609 B1 * 6/2003 Soff et al. .................... 514/12

* cited by examiner

Primary Examiner—Jon P. Weber
Assistant Examiner—Anand Desai
(74) Attorney, Agent, or Firm—Rothwell, Figg, Ernst & Manbeck, P.C.

(57) ABSTRACT

Here is described the use of angiostatin or its fragments to prepare a drug active against pathologies where is beneficial to obtain the inhibition of the migration, activation and release of active molecules from leucocyte of myeloid origin.

3 Claims, 5 Drawing Sheets

MOLECULES WITH ANTI-INFLAMMATORY ACTIVITY

The present invention concerns the use of angiostatin and its active fragments to treat all the pathologic conditions involving an excessive or deregulated activation of leucocytes of myeloid origins, or where it is desirable to inhibit the chemotactic migration or the release of active chemical species. These conditions are mainly reportable to inflammatory conditions of different origins.

Angiostatin is a circulating proteolytic cleavage product of plasminogen that can suppress the growth of a variety of tumors through an as yet not completely defined mechanism. Several studies have proposed that angiostatin induces selective inhibition of endothelial cell proliferation, migration, induction of endothelial cell cycle arrest and apoptosis [Cao, 1996 #2497; Lucas, 1998 #2499; Lu, 1999 #2498; Griscelli, 1998 #2238].

Even if the obvious target of anti-angiogenic compounds are endothelial cells, an increasing body of evidence indicates that cells from the natural immune system such as monocyte/macrophages are important regulators of angiogenesis [Sunderkotter, 1994 #1138; Polverini, 1997 #1963]. Granulocytes, whose role is frequently underestimated, also appear to play a primary role in the initial phases of the angiogenic process [Cassatella, 1999 #2671; Kasama, 2000 #2670]. Recent studies on the HIV-Tat protein have shown that the angiogenic potential of this molecule is linked not only to VEGF mimicry, but also to recruitment of granulocytes in vitro and in vivo via a chemokine-like domain of this molecule [Benelli, 2000 #2680].

Although the precise role of neutrophils in tumor development is still uncertain as their contribution may be time-restricted, they could induce tumor growth by direct promotion of vessel generation under both physiological (wound healing) and pathological (cancer, psoriasis) conditions. To date, studies on the effects of angiostatin have been limited to vascular cells (endothelial and smooth muscle cells); its role in phagocyte control has never been investigated.

The inventors have found that angiostatin is a strong inhibitor of neutrophil migration, activation and degranulation, as well as of neutrophil-mediated angiogenesis.

Angiostatin reduced by about 20–30% the migration of primary monocytes towards chemotactic stimuli as fMLP, MCP-1 and HIV-Tat, but was much more efficient as granulocyte inhibitor. The activity of angiostatin on PMN has been confirmed by dose-dependence studies using chemoattractants as IL-8 (50 ng/ml), MIP-2 (200 ng/ml), Tat (1 $\mu$M) or fMLP ($10^{-7}$M) able to induce a high chemotactic response (FIG. 1). The addition of angiostatin caused a strong inhibition of migration peaking at the concentration of 1.25–2.5 $\mu$g/ml (p$\leq$0.0053 Student T test as compared to controls). Higher doses of angiostatin (5–10 $\mu$g/ml) were less effective. Also the chemotaxis induced by the phorbol ester TPA (200 ng/ml) was dose-dependently inhibited by angiostatin (FIG. 1). The inhibition of TPA induced migration suggests a possible modulation of the MAP-kinase pathway downstream PKC (28), a signal transduction pathway known to be involved in granulocyte migration. Several different angiostatin preparations have shown the same biological properties (FIG. 1). On the contrary, intact plasminogen has not shown any inhibitory potential.

Additional studies on PMN migration have been performed using GRO-alpha and MIP-2 as chemoattractants, as these chemokines selectively engage the CXCR2 (while IL-8 targets both CXCR1 and CXCR2). Even in these experimental settings angiostatin showed an inhibitory activity on granulocyte migration, according to the doses and responses observed with the other chemoattractants.

As a further proof to in vitro data, the inventors have tested angiostatin in the matrigel sponge model in vivo (29). Previous observations indicated that the majority of growth factors do not act only on endothelial cells, but in most cases (i.e. HIV-Tat, VEGF and Kaposi sarcoma cells supernatants) are able to recruit also mesenchymal cells and phagocytes in matrigel implants (23,30). The addition of IL-8 along with matrigel causes a strong angiogenic reaction, characterized by abundant dilated neovascular formations, and granulocyte infiltration. The addition of angiostatin to the sponges, in addition to a total, block of the angiogenesis induced by IL-8, MIP-2, GRO-alfa or LPS (FIG. 2b), drastically reduced the total number of cells inside the implant, where, instead of vessels, can be observed only small lacunae without endothelial lining (FIG. 3b,f,h). Using an anti-myeloperoxidase antibody the inventors have also shown that leucocytes infiltrating the IL-8 containing gels are neutrophil granulocytes and monocytes (FIG. 3c). The invasion of degranulating neutrophils, observed by electron microscopy analysis, often precedes and leads the monocyte and endothelial cell invasion of the sponge (23,30). The fundamental role of neutrophils in angiogenesis induction has been confirmed in neutrophil-depleted mice, where matrigel implants enriched with chemokines are not vascularized (FIG. 2a).

The neutrophil degranulation observed in matrigel sponges (23,30) suggests an acivated phenotype for these cells during the neoangiogenic process. Angiostatin (MTT assay) can inhibit by 80% the mitochondrial activity of IL-8 stimulated granulocytes and by 63% the fMLP induced activation (FIG. 4b). Membrane-associated ATP synthase and angiomotin have been respectively indicated as putative angiostatin receptors on endothelial cells, the RT-PCR of these receptors on PMN and on other cells of the myeloid lineage have shown the expression of both receptors. ATP-synthase has also been detected by FACS analysis of neutrophils by a specific antibody. Consequently these receptors can mediate the observed inhibitory effects (FIG. 4a).

Angiostatin has also been successfully used to block HIV-Tat induced PMN recruitment and angiogenesis. The full-length 1–101 amino-acid HIV-1 Tat protein induces a strong neutrophil chemotactic response in vitro. The addition of angiostatin to the neutrophils in the upper chamber of the microwells caused a significant decrease in cell migration to Tat (FIG. 5). This inhibition appeared again to be strictly dose dependent, with a maximal activity at 2.5 $\mu$g/ml. HIV-Tat harbors several active domains interacting with cell surface receptors, among these the RGD sequence which binds avb3 and avb5 integrin (7,8), the basic domain which binds and activates flk-1/VEGFR2 (15) and the cysteine-core domain with chemokine-like activity. To examine the role of the chemokine-like properties of Tat in the inhibitory activity of angiostatin, a peptide containing only the chemokine-like domain of Tat was used (CysL24–51). Similar to what observed with whole Tat, the CysL24–51 peptide strongly induced neutrophil migration which was again inhibited by angiostatin (FIG. 5). A maximal level of activity at 2.5 $\mu$g/ml was observed, and again higher or lower doses showed a reduced effect.

The inclusion of Tat in matrigel sponges injected in vivo results in a strong, rapid angiogenic response (FIG. 5 lower panel). The addition of angiostatin along with Tat completely abolished the angiogenic response to Tat, bringing the hemoglobin levels in the gels (a quantitative indicator of vascularization) to baseline levels. Angiostatin alone was not angiogenic. Histological analysis of the implants showed a strong, hemorrhagic angiogenesis with massive cell infiltration in the implants with Tat, while Tat implants also containing angiostatin had low cellularity and no vessels.

All these experimental evidences demonstrate that angiostatin, besides the well known antiangiogenic activity, can reduce granulocyte recruitment and activation, reducing the local production and release of reactive oxigen species.

Accordingly, object of this invention is a method for treating a pathologic condition in which the recruitment and/or the activation of myeloid leucocytes, especially polymorphonucleate granulocytes, are involved, which comprises administering to an animal, preferably a human subject in need of such a treatment, an effective amount of angiostatin or a biologically active fragment thereof.

The term "biologically active fragments" indicates peptides derived from angiostatin, which could be modified in the sequence by substitution or addition of one or more amino acids with other natural or synthetic ones, maintaining or improving the biological and pharmacological properties of the full length protein. The active fragments will preferentially contain the first three "kringles" of angiostatin.

According to a preferred embodiment of the invention, angiostatin or active fragments thereof are used in the treatment of inflammatory pathologies.

The dose schedule of angiostatin according to this invention will be adapted to the pathology, the clinical condition of the patient, and to the route of administeration. As a general indication, the compounds will be used in dosages ranging from 0.5 mg/Kg to 500 mg/Kg, preferably 1 to 100 mg/Kg, more preferably from 2 to 50 mg/Kg, once or twice a day. The route of administration for the present invention include parenteral (subcutaneous, intramuscular, intravenous, intradermic), oral, nasal, rectal, ophtalmic and topic applications. The drug will be administered as solution, suspension, infusion, capsule, tablet, injectable, spray, creme, emulsion, gel, drops, and can be prepared by conventional procedures, for example as described in Remington's Pharmaceutical Sciences Handbook, Mack Pub. Co., NY, USA, XVII Ed.

Figure 1:
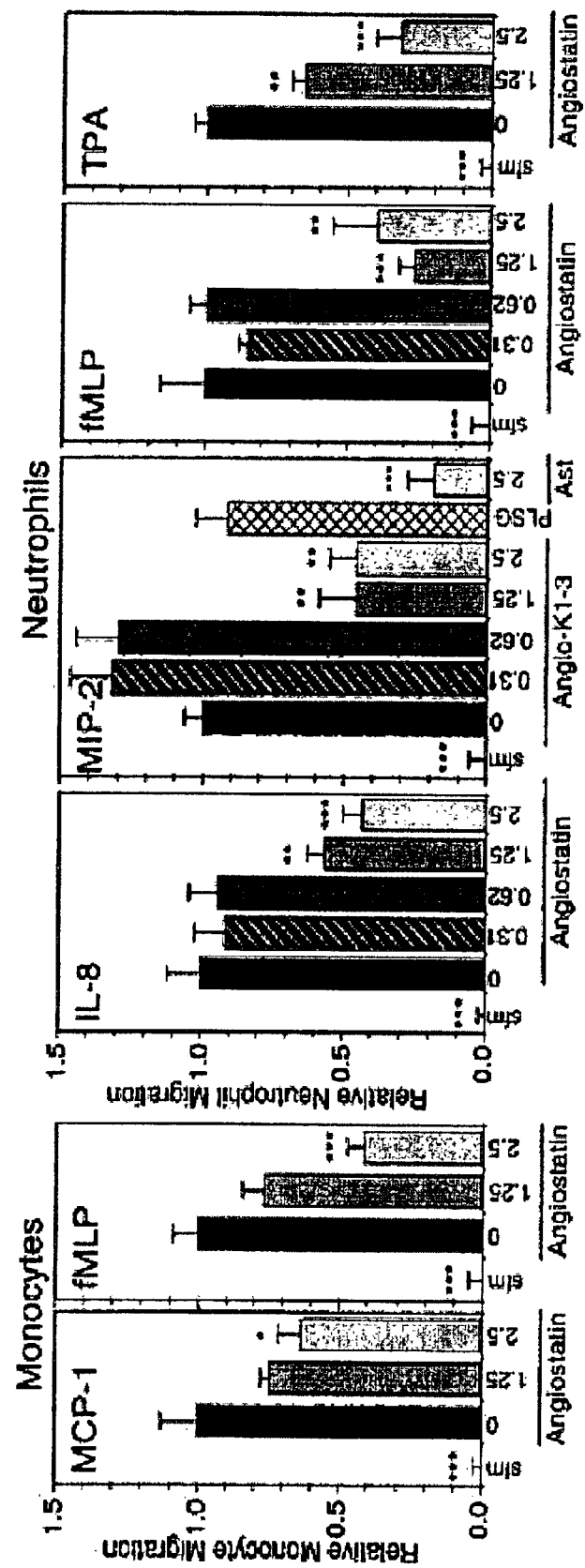
FIG. 1

Inhibition of monocyte or neutrophil migration to the chemoattractants IL-8 (50 ng/ml), MIP-2 (200 ng/ml), fMLP (10−7M), or TPA (200 ng/ml) (as indicated in each panel) by increasing doses of angiostatin (Ast) or the angiostatin-K1–3 fragment (Angio-K 1–3) of plasminogen (as indicated on the abscissa, doses are in $\mu$g/ml). Plasminogen alone (PLSG) at 5.7 $\mu$g/ml (equimolar relative to 2.5 $\mu$g/ml angiostatin) had little effect. Data from independent experiments were normalized and pooled by subtraction of mean random background migration to serum-free medium (sfm), and given relative to mean positive controls (chemoattractant in the absence of inhibitor). Means ± standard errors are shown, asterisks indicate significant inhibition of migration relative to positive controls by ANOVA, with *=p<0.0001; =p<0.01; *=p<0.05. The migration to the positive controls was always significantly higher than that to sfm alone (ANOVA, p<0.0001).

FIG. 2

Vascularization of Matrigel implants after four days in vivo as assessed by measurement of the hemoglobin content in the sponges.

Panel A: The CXCR2 ligands IL-8, MIP-2 and GROα (50 ng/ml) all induced strong angiogenic responses in control animals in vivo. In animals made neutropenic (85% reduction of neutrophils) by injection of the rat anti-mouse Ly-6G (Gr-1) monoclonal antibody, these chemokines produced no angiogenic response.

Panel B: Addition of angiostatin to the gels significantly inhibited angiogenesis in vivo. Nil: hemoglobin content in the absence of an angiogenic factor, angiostatin did not affect angiogenesis per se. Inclusion of IL-8, MIP-2, GROα (50 ng/ml) or LPS (100 ng/ml) (as indicated in each panel) in the gels produced a strong angiogenic response (No Inhibitor). The addition of angiostatin (doses as indicated in $\mu$g|ml or at 2.5 $\mu$g/ml where not indicated) or angiostatin-K 1–3 (Ang-K1–3, 1.9 $\mu$g/ml, equimolar to 2.5 $\mu$g/ml angiostatin) to the gels inhibited the angiogenic response. Plasminogen (PLSG, 5.7 or 11.4 $\mu$g/ml, equimolar to angiostatin at 2.5 o 5 $\mu$g/ml, respectively) did not show any effect. Sub-cutaneous administration of angiostatin-K 1–3 also significantly inhibited angiogenesis.

The data shown are pooled from independent experiments; means±standard errors are shown. Significant inhibition of hemoglobin content relative to positive controls by ANOVA is indicated with asterisks: *=p<0.0001; =p<0.01; *=p<0.05; by t-test (Mann-Whitney) with degree symbols °°°=p<0.002; °°=p<0.02; °=p<0.05.

FIG. 3

Histology of Matrigel pellets implanted in vivo, stained with hematoxylin and eosin (a, b, e-h) or with anti-myeloperoxidase and counter-stained with hematoxylin (c, d). IL-8 (a, c) induced a massive infiltrate of cells, many of which myeloperoxidase positive (c), with large, hemorraghic vessels beginning to penetrate into the matrix. In the presence of angiostatin (2.5 $\mu$g/ml) (b-d) only a few cells penetrate into the matrix, most of these are myeloperoxidase positive, leaving discrete lacunae. MIP-2 induced extensive vascularization of the sponges with large, relatively well organized vessels along with extensive leukocyte infiltration (e). The presence of angiostatin (2.5 $\mu$g/ml) in gels containing MIP-2 essentially blocked the response, with few cells penetrating into the matrigel (f). Matrigel pellets implanted in vivo containing LPS showed a substantial infiltrate with large, poorly organized hemorraghic vessels beginning to penetrate into the matrix (g). LPS with angiostatin (2.5 $\mu$g/ml) again blocked the response, with few cells penetrating into the matrigel (h). The bar is approximately 50 $\mu$m in a, b, e–h and 12.5 $\mu$m in c, d.

FIG. 4

Expression of angiostatin receptors by neutrophils and angiostatin effects on indicators of neutrophil function.

Panel A: RT-PCR of neutrophils and HL60 cells for the cell surface ATP synthase angiostatin receptor. Neutrophils (PMN, >96% neutrophils) showed the expected amplified product similar to control A549 (A549) cells. HL-60 cells, whether or not induced to differentiate with retinoic acid (+RA), also showed strong expression of the ATP synthase mRNA. All samples showed essentially equivalent amplification using primers for b-actin, while no amplification was observed in negative controls (not shown).

Panel B: Flow cytometry analysis of cell surface ATP synthase protein expression on neutrophils, using a monoclonal anti-ATP synthase primary antibody and monoclonal FITC linked anti-mouse secondary antibody. The granulocytes, were >98% positive for cell surface ATP synthase protein (shaded profile) with respect to the negative control (open profile).

Panel C: RT-PCR of neutrophils and HL60 cells for the angiomotin angiostatin receptor. Neutrophils (PMN, >96% neutrophils) showed the expected amplified product similar to control HUVE cells.

B) Neutrophil mitochondrial activity, as measured by the MTT assay, was clearly increased after treatment with fMLP or IL-8 for 24 hours (control, black bars). The presence of angiostatin (Ast, 2.5 µg/ml, white bars) strongly inhibited this activation in both cases. Mean±standard deviations are shown, the differences between angiostatin untreated and treated samples was statistically significant, with p<0.0001 (standard t-test), for both IL-8 and fMLP.

FIG. 5

Inhibition of neutrophil chemotaxis by angiostatin. Tat, CysL24–51 peptide and IL-8 are strong inducers of neutrophils recruitment. When different concentrations of angiostatin were added to the cell suspension an "inverse" bell-shaped dose response curve was observed. With all the chemoattractants tested angiostatin at 2.5 µg/ml proved to be the most effective inhibitory dose. Higher or lower doses of angiostatin had less effect.

Lower panel. Angiostatin inhibits neutrophil-induced angiogenesis in the matrigel sponge model. When angiostatin (2.5 µg/ml) was added to Tat or CysL24–51 peptide-enriched matrigel implants a complete inhibition of the angiogenic response was observed. Data are expressed as the mean of the hemoglobin contents.

EXAMPLES

Human granulocytes were extracted from buffy coats, after mononuclear cell separation by ficoll gradient centrifugation (280×g for 30 min). The pellet containing erythrocytes and granulocytes was diluted in three volumes of lysis solution ($NH_4Cl$ 155 mM, $KHCO_3$, 10 mM, EDTA 0.1 mM, pH 7.4) to eliminate red blood cells. The pellet was eventually washed once in lysis solution and three times in RPMI. The resulting pellet contains 96% neutrophil granulocytes (by FACS analysis of CD15 positive cells).

Monocytes were obtained by a further centrifugation of mononuclear cells in Percoll gradient (density=1062 $g/cm^3$).

Example 1

Chemotaxis Assay

Chemotaxis assay was performed according to Falk, et al. (22) in 48-microwell chemotaxis chambers Costar NUCLEPORE™, Milan, I, EU), using 5 µm pore-size pvp-free polycarbonate filters Costar NUCLEPORE™). The lower compartment of each chamber was filled with 28 µl of chemoattractant; simple RPMI with 0.1% BSA (serum free medium, sfm) was used as control for random unstimulated migration. Cells were pre-incubated with Angiostatin for 30 minutes at the indicated concentrations and then added to the wells in the upper chamber. Each well was filled with 50 µl of a cell suspension containing granulocytes ($5 \times 10^6$ cell/ml) in sfm. Each point was run in sestuplicate. The chambers were incubated for 45 minutes at 37° C. in 5% $CO_2$ humidified atmosphere. The filters were then removed and the cells fixed with 100% ethanol and stained with toluidine blue. Cells that had not migrated were removed from the upper surface of the filter with filter paper. Migration was measured by densitometric analysis. The results are shown in FIG. 1, where it is shown the inhibition of granulocyte and monocyte chemotaxis, towards several chemoattractants, by angiostatin. The migration in the absence of any chemoattractant (sfm) indicates basal random migration. Angiostatin (Ang) causes a significant inhibition of monocyte chemotaxis in response to MCP-1 and fMLP at the dose of 2.5 µg/ml and inhibits the chemotaxis of granulocytes towards IL-8, MIP-2, fMLP and TPA at the doses of 1.25 e 2.5 µg/ml (p always <0.03; Student T test).

Example 2

In Vivo Angiogenesis

The matrigel model of angiogenesis in vivo introduced by Passaniti et al (23) and modified by Albini et al (see 23) was utilized. Either IL-8, MIP-2 or GROa (at 50 ng/ml) or LPS (100 ng/ml) were added to liquid Matrigel containing heparin at 4° C. to a final volume of 0.6 ml. The Matrigel suspension was slowly injected subcutaneously into the flanks of c57 black mice using a cold syringe, in vivo the gel rapidly polymerized to form solid implants. Angiostatin was added directly into the matrigel at the concentration of 2.5 µg/ml, negative controls were Matrigel suspensions without angiogenic factor, with or without angiostatin. After 4 days, gels were collected and subjected to analysis of hemoglobin content. In addition, some samples were paraffin embedded and stained with hematoxylin & eosin for histological analysis or with an anti-myeloperoxidase antibody for histochemical identification of PMN and monocytes/macrophages.

FIG. 2a shows how the proangiogenic activity of control chemokines is mediated by neutrophils recruitment, as neutrophil depleted mice do not vascularize matrigel sponges.

Figure 2:
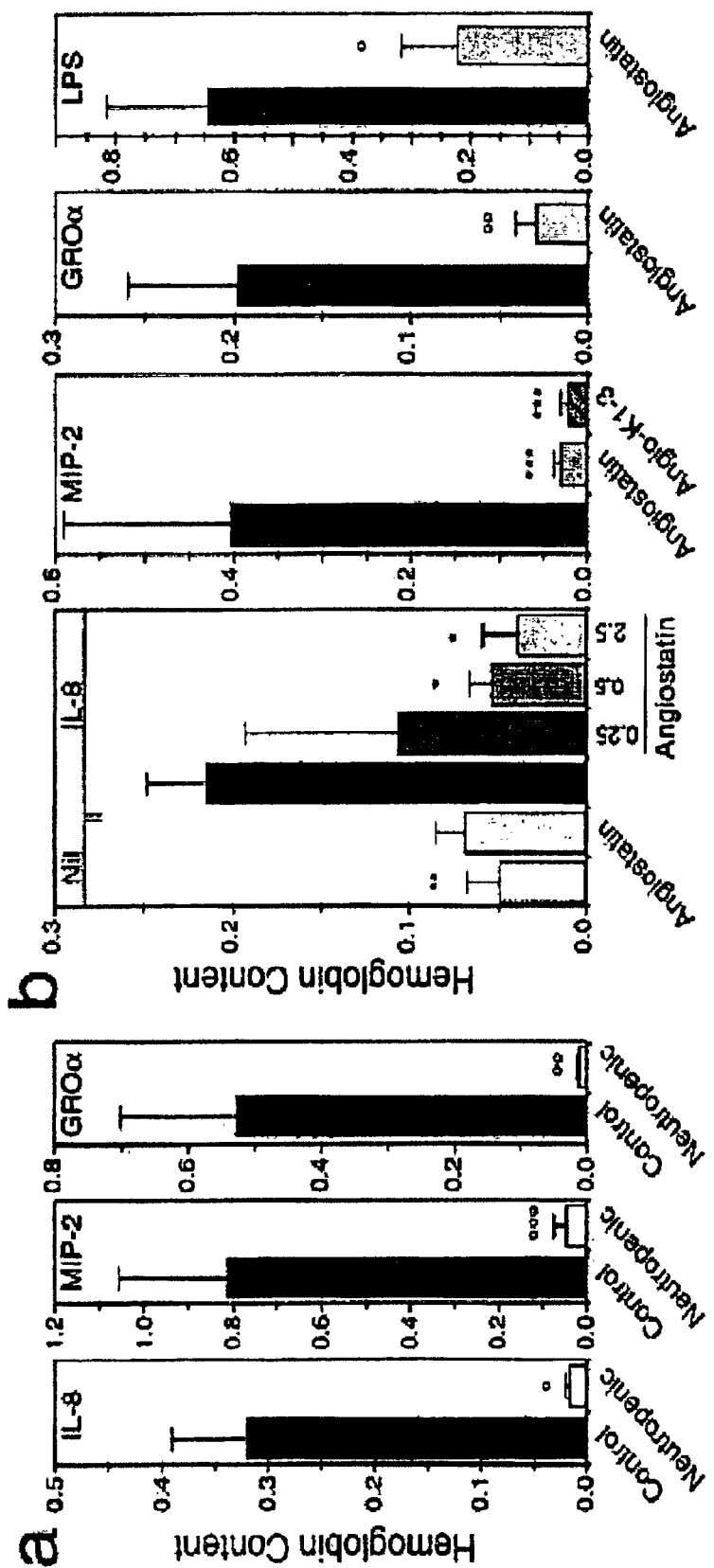

Angiostatin (Ang 2.5 µg/ml), as shown in FIG. 2b show a strong antiangiogenic potential against IL-8, MIP-2 and GRO-alfa-mediated vascularization. Angiostatin displayed its antiangiogenic potential even against the exogenous stimulus LPS, from gram negative bacteria. Graphs in FIG. 2 express the hemoglobin content in mg/dl.

Figure 3:
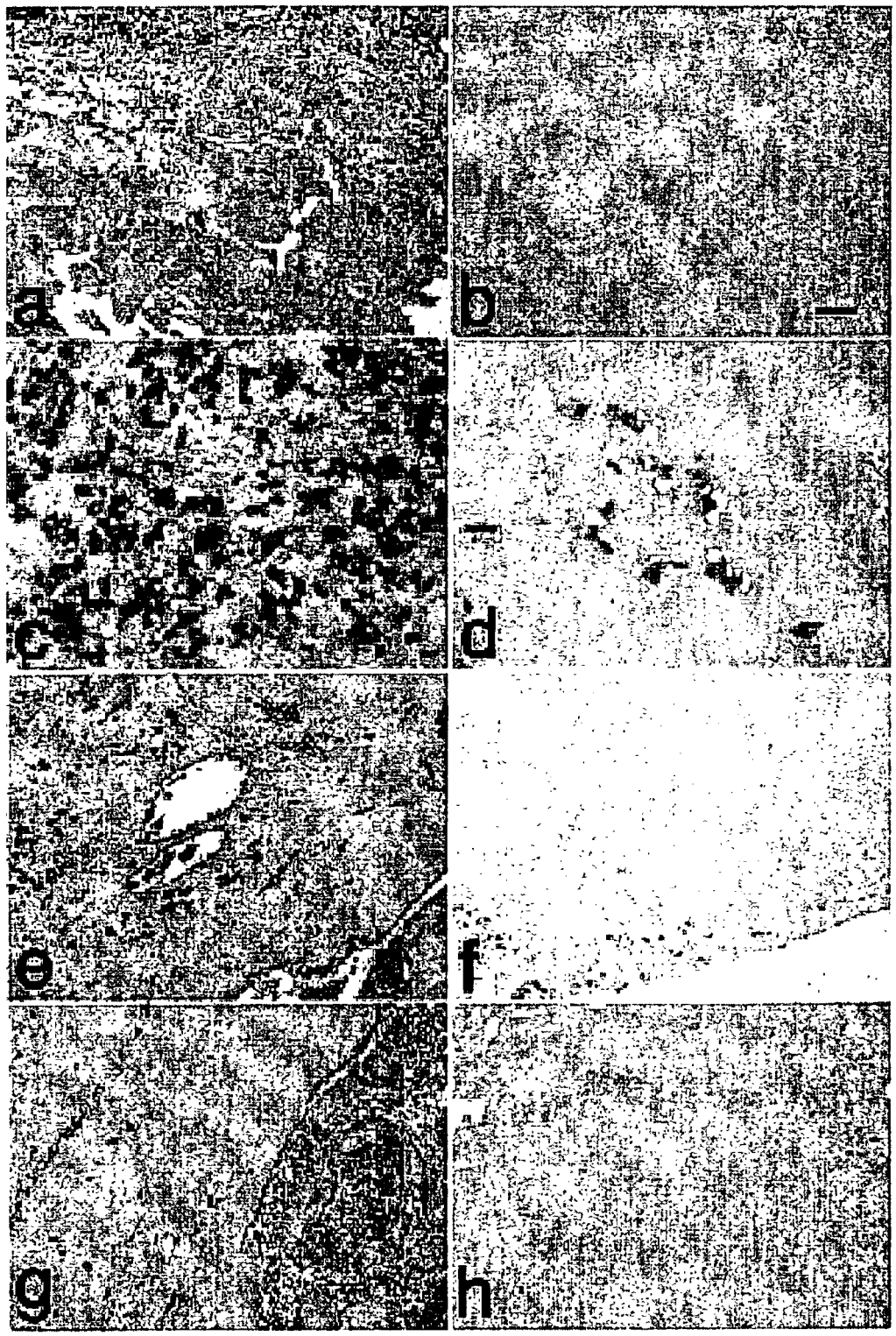

FIG. 3 shows matrigel pellets histology, stained with hematoxylin & eosin (a,b,e,f,g,h) or anti-myeloperoxidase (c,d). IL-8 (a,c) induces a dense inflammatory infiltrate in the gel with large hemorragic vessels. In the presence of angiostatin (b,d) only few myeloperoxidase positive cells and small lacunae are observed. The bar represents 50 µm in a, b, e, f, g, h and 12. 5 µm in c-d.

Example 3

Amplification of Angiostatin Receptors in Granulocytes and MTT Assay

As in endothelial cells angiostatin could use two distinct receptors to exert its inhibitory activity we have tested if PMN expresses the messenger RNA of these receptors. RT-PCR amplification, shown in FIG. 4a, indicates that both membrane associated ATP-synthase and Angiomotin are expressed by granulocytes (ATP-synthase was also detected on PMN surface by specific antibodies). Angiostatin could use both receptors on granulocytes to exert its effects.

Figure 4:
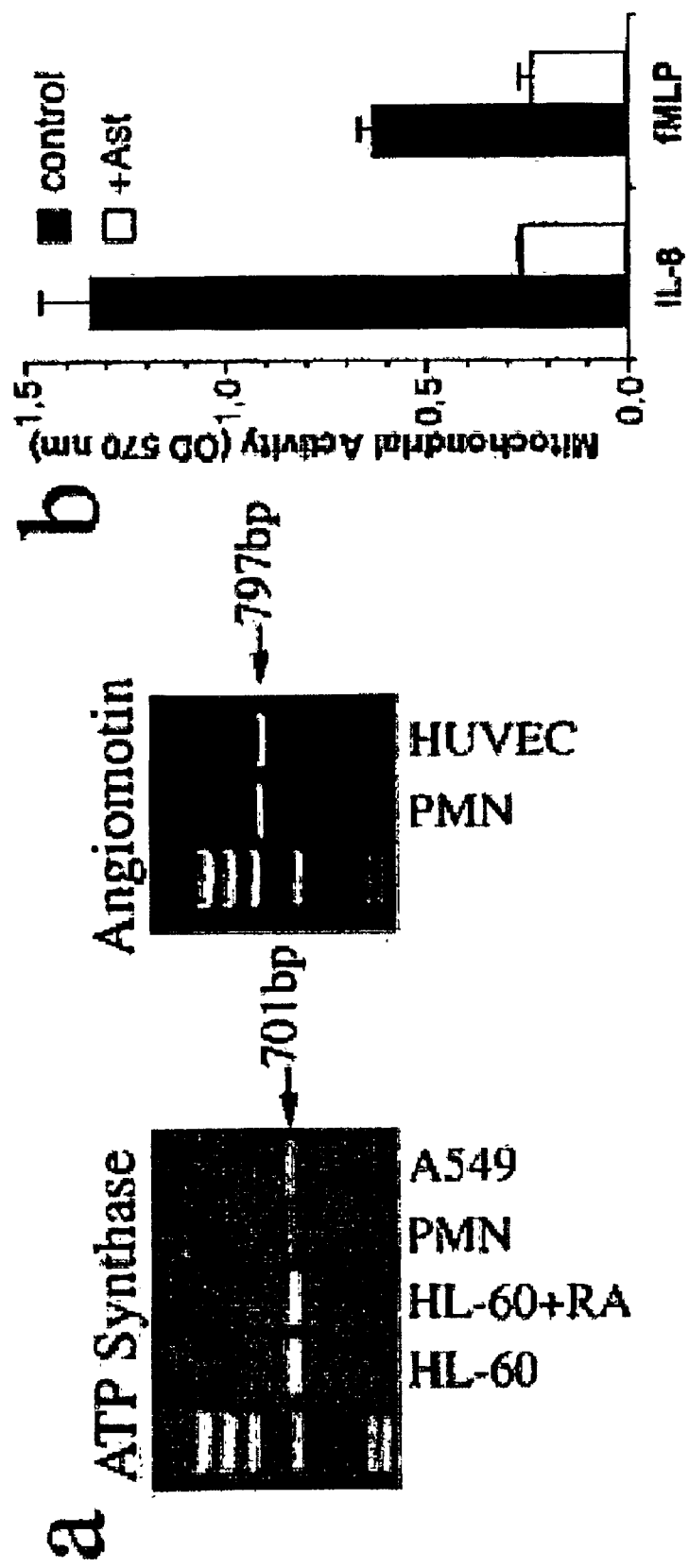
Figure 5:
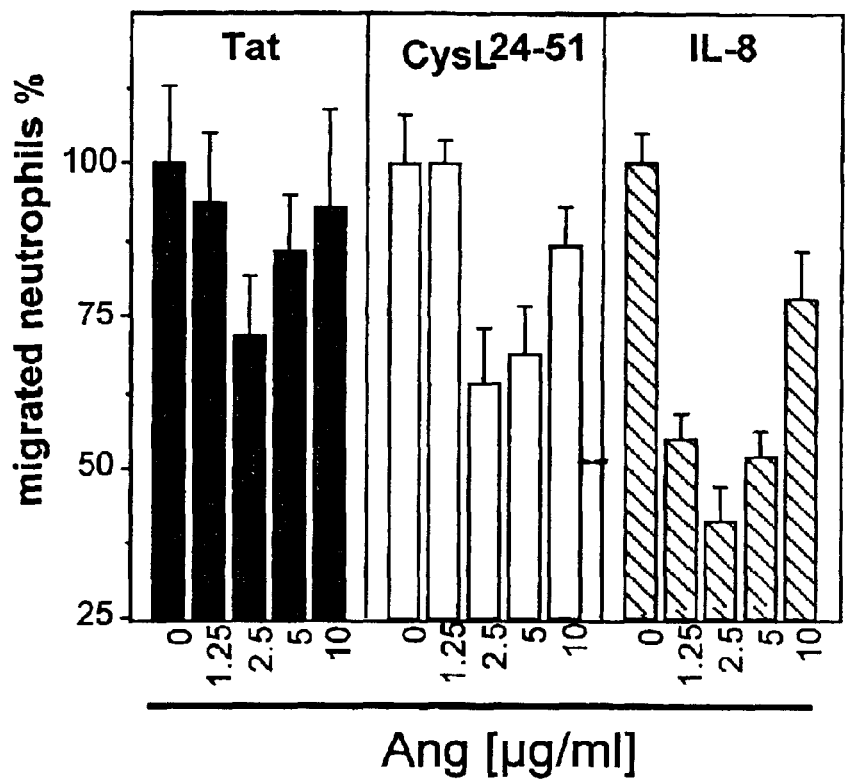
Figure 5:
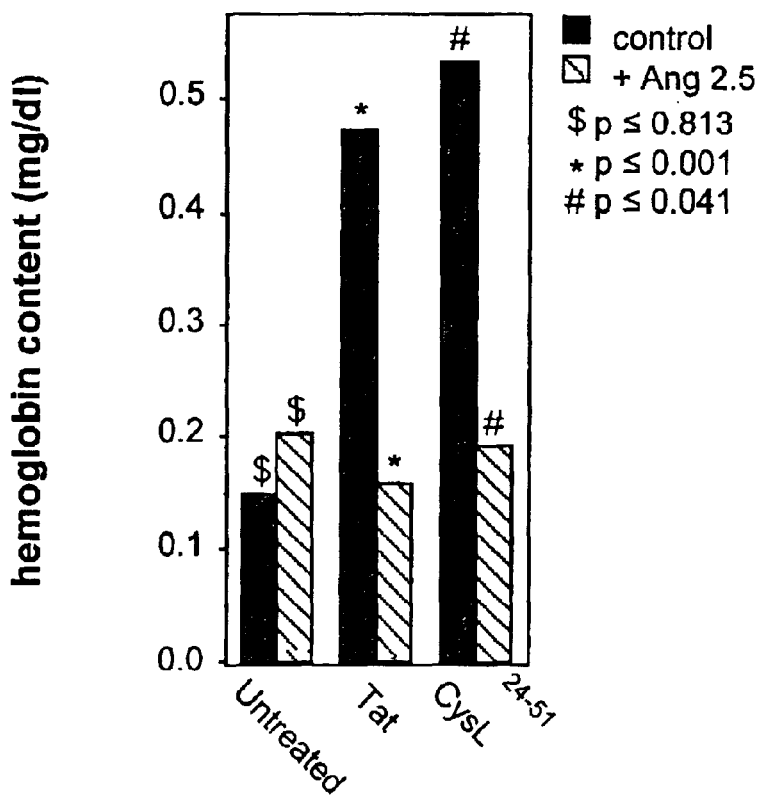

Granulocyte mitochondrial activity was determined using the MTT metabolic assay (24). PMN were seeded into 96-well culture plates, in RPMI 10% FCS in the presence of il-8 (100 ng/ml) or fMLP (10 nm) and incubated for 24 hours. A solution (50 µl) of tetrazolium salt (MTT, 3-[4,5-dimethylthiazol-2-yl]-2,5-diphenyltetrazolium bromide; 2 mg/ml in PBS) preheated at 37° C. was then added to each well and incubated for 4 hours at 37° C. in a humidified 5% $CO_2$ atmosphere. Mitochondria-reduced MTT forms insoluble blue formazan salts, which were solubilized in DMSO and read in a multiwell scanning spectrometer at 540 nm wavelength. As shown in FIG. 4b, the mitochodrial activity of granulocytes is increased after fMLP or IL-8 challenge; angiostatin (Ang 2.5 µl) inhibits both stimuli.

REFERENCES

1. Shanahan, F. and G. C. O'Sullivan. Angiostatin: candidate for molecule of the year! Gastroenterology 108: 1946–8, 1995.

2. O'Reilly, M. S., L. Holmgren, Y. Shing, C. Chen, R. A. Rosenthal, M. Moses, W. S. Lane, Y. Cao, E. H. Sage and J. Folkman. Angiostatin: a novel angiogenesis inhibitor that mediates the suppression of metastases by a Lewis lung carcinoma. Cell 79: 315–28, 1994.

3. Cao, Y., R. W. Ji, D. Davidson, J. Schaller, D. Marti, S. Sohndel, S. G. McCance, M. S. O'Reilly, M. Llinas and J. Folkman. Kringle domains of human angiostatin. Characterization of the anti-proliferative activity on endothelial cells. J Biol Chem 271: 29461–7, 1996.

4. Lucas, R., L. Holmgren, I. Garcia, B. Jimenez, S. J. Mandriota, F. Borlat, B. K. Sim, Z. Wu, G. E. Grau, Y. Shing, G. A. Soff, N. Bouck and M. S. Pepper. Multiple forms of angiostatin induce apoptosis in endothelial cells. Blood 92: 4730–41, 1998.

5. Lu, H., M. Dhanabal, R. Volk, M. J. Waterman, R. Ramchandran, B. Knebelmann, M. Segal and V. P. Sukhatme. Kringle 5 causes cell cycle arrest and apoptosis of endothelial cells. Biochem Biophys Res Commun 258: 668–73, 1999.

6. Walter, J. J. and D. C. Sane. Angiostatin binds to smooth muscle cells in the coronary artery and inhibits smooth muscle cell proliferation and migration In vitro. Arterioscler Thromb Vasc Biol 19: 2041–8, 1999.

7. Sunderkotter, C., K. Steinbrink, M. Goebeler, R. Bhardwaj and C. Sorg. Macrophages and angiogenesis. J Leukoc Biol 55: 410–22, 1994.

8. Polverini, P. J. Role of the macrophage in angiogenesis-dependent diseases. In Regulation of Angiogenesis, Goldberg and Rosen, eds. 1997 Birkhäuser Verlag. Basel.

9. Kobayashi, T., K. Hamano, T. S. Li, T. Katoh, S. Kobayashi, M. Matsuzaki and K. Esato. Enhancement of angiogenesis by the implantation of self bone marrow cells in a rat ischemic heart model. J Surg Res 89: 189–95, 2000.

10. McColley, S. A., V. Stellmach, S. R. Boas, M. Jain and S. E. Crawford. Serum Vascular Endothelial Growth Factor Is Elevated in Cystic Fibrosis and Decreases with Treatment of Acute Pulmonary Exacerbation. Am J Respir Crit Care Med 161: 1877–1880, 2000.

11. McCourt, M., J. H. Wang, S. Sookhai and H. P. Redmond. Proinflammatory mediators stimulate neutrophil-directed angiogenesis. Arch Surg 134: 1325–31; discussion 1331–2, 1999.

12. Michiels, C., T. Arnould and J. Remacle. Endothelial cell responses to hypoxia: initiation of a cascade of cellular interactions. Biochim Biophys Acta 1497: 1–10, 2000.

13. Patterson, B. C. and Q. A. Sang. Angiostatin-converting enzyme activities of human matrilysin (MMP-7) and gelatinase B/type IV collagenase (MMP-9). J Biol Chem 272: 28823–5, 1997.

14. O'Reilly, M. S., D. Wiederschain, W. Stetler-Stevenson, J. Folkman and M. A. Moses. Regulation of angiostatin production by matrix metalloproteinase-2 in a model of concomitant resistance. J Biol Chem 274: 29568–71, 1999.

15. Dong, Z., R. Kumar, X. Yang and I. J. Fidler. Macrophage-derived metalloelastase is responsible for the generation of angiostatin in Lewis lung carcinoma. Cell 88: 801–10, 1997.

16. Cassatella, M. A., S. Gasperini and M. P. Russo. Cytokine expression and release by neutrophils. Ann N Y Acad Sci 832: 233–42, 1997.

17. Kitadai, Y., Y. Takahashi, K. Haruma, K. Naka, K. Sumii, H. Yokotani, W. Yasui, N. Mukaida, Y. Ohmoto, G. Kajiyama, I. J. Fidler and E. Tahara. Transfection of interleukin-8 increases angiogenesis and tumorigenesis of human gastric carcinoma cells in nude mice. Br J Cancer 81: 647–53, 1999.

18. Chen, Z., P. S. Malhotra, G. R. Thomas, F. G. Ondrey, D. C. Duffey, C. W. Smith, I. Enamorado, N. T. Yeh, G. S. Kroog, S. Rudy, L. McCullagh, S. Mousa, M. Quezado, L. L. Herscher and C. Van Waes. Expression of proinflammatory and proangiogenic cytokines in patients with head and neck cancer. Clin Cancer Res 5: 1369–79, 1999.

19. Miller, L. J., S. H. Kurtzman, Y. Wang, K. H. Anderson, R. R. Lindquist and D. L. Kreutzer. Expression of interleukin-8 receptors on tumor cells and vascular endothelial cells in human breast cancer tissue. Anticancer Res 18: 77–81, 1998.

20. Baggiolini, M., P. Loetscher and B. Moser. Interleukin-8 and the chemokine family. Int J Immunopharmacol 17: 103–8, 1995.

21. Falk, W., R. J. Goodwin and E. Leonard. A 48-well microchemotaxis assembly for rapid and accurate measurement of leukocyte migration. J. Immunol. Methods 33: 239–247, 1980.

22. Passaniti, A., R. M. Taylor, R. Pili, Y. Guo, P. V. Long and J. A. Haney. A simple, quantitative method for assessing angiogenesis and antiangiogenic agents using reconstituted basement membrane, heparin, and fibroblast growth factor. Lab. Invest. 67: 519–528, 1992.

23. Albini, A., G. Fontanini, L. Masiello, C. Tacchetti, D. Bigini, P. Luzzi, D. M. Noonan and W. G. Stetler-Stevenson. Angiogenic potential in vivo by Kaposi sarcoma cell-free supernatants and HIV1-tat product: inhibition of KS-like lesions by TIMP-2. AIDS 8: 1237–1244, 1994.

24. Carmichael, J., W. G. Degraff, A. F. Gazdar, J. D. Minna and J. B. Mitchell. Evaluation of a tetrazolium-based semi-automated colorimetric assay: assessment of chemotherapy testing. Cancer Res. 47: 936–943, 1987.

25. Cassatella, M. A., F. Bazzoni, M. Ceska, I. Ferro, M. Baggiolini and G. Berton. IL-8 production by human polimorphonuclear leukocytes. The chemoattractant fMLP induces the gene expression and release of IL-8 through a Pertussin Toxin-sensitive pathway. J. Immunol 148: 3216–3220, 1992.

26. Cassatella, M. A. The production of cytokines by polymorphonuclear neutrophils. Immunology Today 16: 21–6, 1995.

27. Fidler, I. J. Angiogenesis and cancer metastasis. Cancer J Sci Am 6 Suppl 2: S134–41, 2000.

28. Redlitz, A., G. Daum and E. H. Sage. Angiostatin diminishes activation of the mitogen-activated protein kinases ERK-1 and ERK-2 in human dermal microvascular endothelial cells. J Vasc Res 36: 28–34, 1999.

29. Albini, A., R. Soldi, D. Giunciuglio, E. Giraudo, R. Benelli, L. Primo, D. Noonan, M. Salio, G. Camussi, W. Rockl and F. Bussolino. The angiogenesis induced by HIV-1 Tat is mediated by the flk-1/KDR receptor on vascular endothelial cells. Nat. Med. 2: 1371–1375, 1996.

30. Benelli, R., A. Barbero, S. Ferrini, P. Scapini, M. Cassatella, F. Bussolino, C. Tacchetti, D. Noonan and A. Albini. Human immunodeficiency virus transactivator protein (Tat) stimulates chemotaxis, calcium mobilization and activation of human polymorphonuclear cells: implications for Tat-mediated pathogenesis. J. Infect. Dis. 182: in press, 2000.

31. Cassatella, M. A. Neutrophil-derived proteins: selling cytokines by the pound. Adv Immunol 73: 369–509, 1999.

32. Gaudry, M., O. Bregerie, V. Andrieu, J. ElBenna, M. A. Pocidalo and J. Hakim. Intracellular pool of vascular 33. Luo, J., J. Lin, G. Paranya and J. Bischoff. Angiostatin upregulates E-selectin in proliferating endothelial cells. Biochem Biophys Res Commun 245: 906–11, 1998.
34. Claesson Welsh, L., M. Welsh, N. Ito, B. Anand Apte, S. Soker, B. Zetter, M. O'Reilly and J. Folkman. Angiostatin induces endothelial cell apoptosis and activation of focal adhesion kinase independently of the integrin-binding motif RGD. Proc Natl Acad Sci USA 95: 5579–83, 1998.
35. Stack, M. S., S. Gately, L. M. Bafetti, J. J. Enghild and G. A. Soff. Angiostatin inhibits endothelial and melanoma cellular invasion by blocking matrix-enhanced plasminogen activation. Biochem J 340: 77–84, 1999.
36. Liu, J., B. Razani, S. Tang, B. I. Terman, J. A. Ware and M. P. Lisanti. Angiogenesis activators and inhibitors differentially regulate caveolin-1 expression and caveolae formation in vascular endothelial cells. Angiogenesis inhibitors block vascular endothelial growth factor-induced down-regulation of caveolin-1. J Biol Chem 274: 15781–5, 1999.
37. Moser, T. L., M. S. Stack, I. Asplin, J. J. Enghild, P. Hojrup, L. Everitt, S. Hubchak, H. W. Schnaper and S. V. Pizzo. Angiostatin binds ATP synthase on the surface of human endothelial cells. Proc Natl Acad Sci USA 96: 2811–6, 1999.
38. Cornelius, L. A., L. C. Nehring, E. Harding, M. Bolanowski, H. G. Welgus, D. K. Kobayashi, R. A. Pierce and S. D. Shapiro. Matrix metalloproteinases generate angiostatin: effects on neovascularization. J Immunol 161: 6845–52, 1998.
39. Gately, S., P. Twardowski, M. S. Stack, M. Patrick, L. Boggio, D. L. Cundiff, H. W. Schnaper, L. Madison, O. Volpert, N. Bouck, J. Enghild, H. C. Kwaan and G. A. Soff. Human prostate carcinoma cells express enzymatic activity that converts human plasminogen to the angiogenesis inhibitor, angiostatin. Cancer Res 56: 4887–90, 1996.
40. Heidtmann, H. H., D. M. Nettelbeck, A. Mingels, R. Jager, H. G. Welker and R. E. Kontermann. Generation of angiostatin-like fragments from plasminogen by prostate-specific antigen. Br J Cancer 81: 1269–73, 1999.
41. Lijnen, H. R., F. Ugwu, A. Bini and D. Collen. Generation of an angiostatin-like fragment from plasminogen by stromelysin-1 (MMP-3). Biochemistry 37: 4699–702, 1998.
42. Morikawa, W., K. Yamamoto, S. Ishikawa, S. Takemoto, M. Ono, J. Fukushi, S. Naito, C. Nozaki, S. Iwanaga and M. Kuwano. Angiostatin generation by cathepsin D secreted by human prostate carcinoma cells. J Biol Chem 2000.
43. Falcone, D. J., K. M. Khan, T. Layne and L. Fernandes. Macrophage formation of angiostatin during inflammation. A byproduct of the activation of plasminogen. J Biol Chem 273: 31480–5, 1998.

What is claimed is:

1. A method for treating an acute or an angiogenesis-independent inflammatory state in which recruitment and/or activation of myeloid leukocytes are involved, which method comprises administering to a subject in need of such a treatment, an effective amount of angiostatin or a biologically active fragment comprising the first three kringles of the angiostatin molecule.

2. A method according to claim 1, wherein the myeloid leukocytes are selected from the group consisting of PMN granulocytes, monocytes and macrophages.

3. The method of claim 1, wherein the myeloid leukocytes are polymorphonucleate granulocytes.

* * * * *

UNITED STATES PATENT AND TRADEMARK OFFICE
CERTIFICATE OF CORRECTION

PATENT NO. : 6,815,422 B2  Page 1 of 1
APPLICATION NO. : 10/255096
DATED : November 9, 2004
INVENTOR(S) : Adriana Albini et al.

It is certified that error appears in the above-identified patent and that said Letters Patent is hereby corrected as shown below:

On the Title page, Item -73-, in Assignee list, after "Centro Biotechnologie Avanzate, Genoa (IT)", insert --Istituto Nazionale per la Ricerca sul Cancro, Genoa (IT)--

Signed and Sealed this

Twenty-second Day of July, 2008

JON W. DUDAS
*Director of the United States Patent and Trademark Office*